US011721416B2

United States Patent
De Melo Oliveira et al.

(10) Patent No.: US 11,721,416 B2
(45) Date of Patent: Aug. 8, 2023

(54) SYSTEM AND METHOD FOR EXPANDING SEARCH QUERIES USING CLINICAL CONTEXT INFORMATION

(71) Applicant: KONINKLIJKE PHILIPS N.V., Eindhoven (NL)

(72) Inventors: Lucas De Melo Oliveira, Wilmington, MA (US); Gabriel Ryan Mankovich, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 433 days.

(21) Appl. No.: 16/633,274

(22) PCT Filed: Jul. 24, 2018

(86) PCT No.: PCT/EP2018/069963
§ 371 (c)(1),
(2) Date: Jan. 23, 2020

(87) PCT Pub. No.: WO2019/020587
PCT Pub. Date: Jan. 31, 2019

(65) Prior Publication Data
US 2021/0158908 A1    May 27, 2021

Related U.S. Application Data

(60) Provisional application No. 62/538,005, filed on Jul. 28, 2017.

(51) Int. Cl.
*G06F 16/24* (2019.01)
*G16H 10/60* (2018.01)
(Continued)

(52) U.S. Cl.
CPC ........... *G16H 10/60* (2018.01); *G06F 16/243* (2019.01); *G06F 16/24534* (2019.01); *G06F 16/24553* (2019.01); *G16H 70/20* (2018.01)

(58) Field of Classification Search
CPC ............ G06F 16/243; G06F 16/24553; G06F 16/24534; G16H 70/20
See application file for complete search history.

(56) References Cited

U.S. PATENT DOCUMENTS

| 7,034,691 | B1 * | 4/2006 | Rapaport | G16H 10/20 600/300 |
| 7,436,311 | B2 * | 10/2008 | Rapaport | G16H 80/00 600/300 |

(Continued)

FOREIGN PATENT DOCUMENTS

| EP | 2283442 A1 * | 2/2011 |
| WO | 2008085857 A2 | 7/2008 |

OTHER PUBLICATIONS

Gulab et al.; "A Framework for Evaluating Automatic Indexing or Classification in the Context of Retrieval", Wiley Online 2015.*

(Continued)

*Primary Examiner* — Daniel A Kuddus

(57) ABSTRACT

A system (400) configured to generate an expanded query for an electronic health database, the system comprising: a user interface (410) configured to receive a query comprising a search string and information about a clinical context in which the search is being performed; and a processor (460) comprising: (i) a model creation module (420) configured to generate a clinical information model comprising one or more clinical concepts; (ii) a prioritization module (430) configured to prioritize the one or more clinical concepts identified in the generated clinical information model based on the received information about the clinical context in which the search is being performed and a clinical guideline or management plan for the patient; (iii) a query expansion module (440) configured to create an expanded query using the prioritized clinical concepts; and (iv) a query (Continued)

module (450) configured to query the electronic health database using the expanded query.

16 Claims, 4 Drawing Sheets

(51) Int. Cl.
    *G16H 70/20*     (2018.01)
    *G06F 16/242*     (2019.01)
    *G06F 16/2455*     (2019.01)
    *G06F 16/2453*     (2019.01)

(56) References Cited

U.S. PATENT DOCUMENTS

| | | | |
|---|---|---|---|
| 8,239,216 B2 | 8/2012 | McCallie, Jr. et al. | |
| 2006/0161457 A1* | 7/2006 | Rapaport | G16H 10/20 705/2 |
| 2008/0097791 A1* | 4/2008 | Alsafadi | G16H 50/20 707/999.1 |
| 2010/0131482 A1 | 5/2010 | Linthicum et al. | |
| 2011/0004588 A1 | 1/2011 | Leitersdorf et al. | |
| 2011/0066425 A1* | 3/2011 | Hudgins | G06Q 10/10 704/10 |
| 2013/0185099 A1* | 7/2013 | Bucur | G16H 10/60 705/2 |
| 2014/0129246 A1* | 5/2014 | Vdovjak | G16H 10/60 705/2 |
| 2014/0350954 A1 | 11/2014 | Ellis et al. | |
| 2014/0365243 A1* | 12/2014 | Varadan | G16H 10/60 705/3 |
| 2016/0314278 A1* | 10/2016 | Mabotuwana | G16H 30/40 |
| 2016/0365243 A1* | 12/2016 | Hirose | H01L 21/02211 |

OTHER PUBLICATIONS

Gulab et al.; "A Framework for Evaluating Automatic Indexing or Classification in the Context of Retrieval", Wiley Online. (Year: 2015).*

International Search Report and Written Opinion for International Application No. PCT/EP2018/069963, Filed Jul. 24, 2018, 14 pages.

Barathi, et al., "Ontology Based Query Expansion Using Word Sense Disambiguation", International Journal of Computer Science and Information Security (IJCSIS), vol. 7, No. 2, Feb. 2010, pp. 22-27.

Jain, et al., "Enhancing electronic medical record retrieval through semantic query expansion", Inf. Syst E-Bus Manage (2012) 10:165-181.

* cited by examiner

SYSTEM AND METHOD FOR EXPANDING SEARCH QUERIES USING CLINICAL CONTEXT INFORMATION

RELATED APPLICATIONS

This application is the U.S. National Phase application under 35 U.S.C. § 371 of International Application No. PCT/EP2018/069963, filed on Jul. 24, 2018, which claims the benefit of Provisional Application Ser. No. 62/538,005, filed Jul. 28, 2017. These applications are hereby incorporated by reference herein, for all purposes.

TECHNICAL FIELD

The present disclosure is directed generally to methods and systems for querying electronic health record databases.

BACKGROUND

Free-text medical records are often available in an electronic form and are usually part of the medical records of a patient, therefore playing a critical role in clinical practice. Typically, these handwritten notes communicate findings, assumptions, uncertainties, conclusions, and/or recommendations made by a reporting physician to other clinicians involved in a patient's case. In addition, patients are increasingly interested in having access to their medical record. These records provide information about a patient's condition or treatment, and contain a wealth of information far beyond the immediate clinical use. For example, administrators may utilize these records to obtain performance measures while researchers may search the data for cohort identification.

However, simple text searching is often not effective. The complex manner in which clinical information is reported in free text clinical documents limits their utilization. As just one example, a query for patients with "heart disease" may return many false positives because this phrase is often negated in notes (e.g., "no history of heart disease"). The same query may also result in many false negatives because it does not capture variations such as "cardiovascular disease" or "vascular disease" or "arteriosclerosis."

There are several approaches in the art of information retrieval (IR) that purports to improve the quality and reliability of clinical domain search. For example, query expansion (QE) is the process of modifying or reformulating an original query to improve retrieval performance and obtain additional relevant documents, typically by expanding the original query with additional relevant terms and reweighting the terms in the expanded query. Synonym-based expansion, topic model-based expansion, and predication-based model expansion are examples of QE techniques.

Although traditional search expansion methods such as synonym-base and ontology-base increase the coverage of a free-text search, they are unable to account for the clinical context within which the search is made, and thus result in a significant number of false positives and false negatives.

SUMMARY

There is a continued need for improved query expansion methods to identify relevant search results in free-text clinical documents.

The present disclosure is directed to inventive methods and systems for searching free-text clinical documents. Various embodiments and implementations herein are directed to a query expansion system employing a multi-level clinical context model that contains patient clinical context, clinical knowledge, and clinical workflow information. The system receives a query string and processes the string using natural-language processing techniques in order to link the terms to existing clinical concepts. The system considers the workflow in which the search is being performed (e.g., cardiology workflow, urology workflow, etc.) in order to rank the list of clinical concepts. The system also utilizes the clinical guidelines and/or management plan assigned to the patient to further refine the ranked list. The highest ranked terms are then utilized to expand the original query prior to submission to the database. According to an embodiment, the expanded query can be presented to the user for refinement and/or approval prior to execution.

Generally in one aspect, a system for generating an expanded query for an electronic health database is provided. The system includes: a user interface configured to receive a query from a user, wherein the query comprises a search string and information about a clinical context in which the search is being performed; and a processor comprising: (i) a model creation module configured to generate a clinical information model comprising information from one or more clinical documents for one or more patients, wherein the information comprises one or more clinical concepts; (ii) a prioritization module configured to prioritize the one or more clinical concepts identified in the generated clinical information model based on at least the received information about the clinical context in which the search is being performed and a clinical guideline or management plan for the patient, wherein clinical concepts related to the clinical context and/or the clinical guideline or management plan are prioritized higher than clinical concepts unrelated to the clinical context; (iii) a query expansion module configured to create an expanded query using the prioritized one or more clinical concepts; and (iv) a query module configured to query the electronic health database using the expanded query.

According to an embodiment, at least some of the one or more clinical documents are free-text documents.

According to an embodiment, at least some of the one or more clinical documents are structured medical documents.

According to an embodiment, the clinical information model is generated using natural-language processing.

According to an embodiment, the clinical information model is limited to records about a single patient.

According to an embodiment, the query expansion module is configured to expand the query utilizing one or more of synonym-based expansion, topic model-based expansion, and predication-based model expansion.

According to an embodiment, the user interface is further configured to provide the expanded query to a user, and further configured to receive information from the user about the expanded query.

According to an embodiment, the information received from the user modifies the expanded query.

According to an aspect is a method for querying an electronic health database using an expanded query generation system. The method includes the steps of: (i) receiving a query from a user via the user interface, wherein the query comprises a search string and information about a clinical context in which the search is being performed; (ii) generating, by the processor, a clinical information model comprising information from one or more clinical documents for one or more patients, wherein the information comprises one or more clinical concepts; (iii) prioritizing, by the processor, the one or more clinical concepts identified in the generated clinical information model based on at least the received information about the clinical context in which the search is being performed and a clinical guideline or management plan for the patient, wherein clinical concepts related to the clinical context and/or the clinical guideline or management plan are prioritized higher than clinical concepts unrelated to the clinical context; (iv) expanding, by the processor, the query using the prioritized one or more clinical concepts to create an expanded query; and (v) querying the electronic health database using the expanded query.

According to an embodiment, the method further includes the step of providing results of the electronic health database query to the user.

According to an embodiment, the method further includes the steps of providing the expanded query to the user via the user interface; and receiving input from the user regarding the expanded query, wherein the input modifies the expanded query.

In various implementations, a processor or controller may be associated with one or more storage media (generically referred to herein as "memory," e.g., volatile and nonvolatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the embodiments discussed herein. The terms "program" or "computer program" are used herein in a generic sense to refer to any type of computer code (e.g., software or microcode) that can be employed to program one or more processors or controllers.

The term "network" as used herein refers to any interconnection of two or more devices (including controllers or processors) that facilitates the transport of information (e.g. for device control, data storage, data exchange, etc.) between any two or more devices and/or among multiple devices coupled to the network. As should be readily appreciated, various implementations of networks suitable for interconnecting multiple devices may include any of a variety of network topologies and employ any of a variety of communication protocols. Additionally, in various networks according to the present disclosure, any one connection between two devices may represent a dedicated connection between the two systems, or alternatively a non-dedicated connection. In addition to carrying information intended for the two devices, such a non-dedicated connection may carry information not necessarily intended for either of the two devices (e.g., an open network connection). Furthermore, it should be readily appreciated that various networks of devices as discussed herein may employ one or more wireless, wire/cable, and/or fiber optic links to facilitate information transport throughout the network.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the methods and principles described herein will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles disclosed herein.

DETAILED DESCRIPTION OF EMBODIMENTS

The present disclosure describes various embodiments of an automated query expansion system. More generally, Applicant has recognized and appreciated that it would be beneficial to provide a system that more accurately searches free-text clinical records. The system receives a query string from a user and processes the string using natural-language processing techniques in order to link the terms to existing clinical concepts. The system considers the workflow in which the search is being performed in order to rank the list of clinical concepts. The system also utilizes the clinical guidelines and/or management plan assigned to the patient in order to further refine the ranked list. The highest ranked terms are then utilized to expand the original query prior to submission to the database. According to an embodiment, the expanded query can be presented to the user for refinement and/or approval prior to execution.

Figure 1:
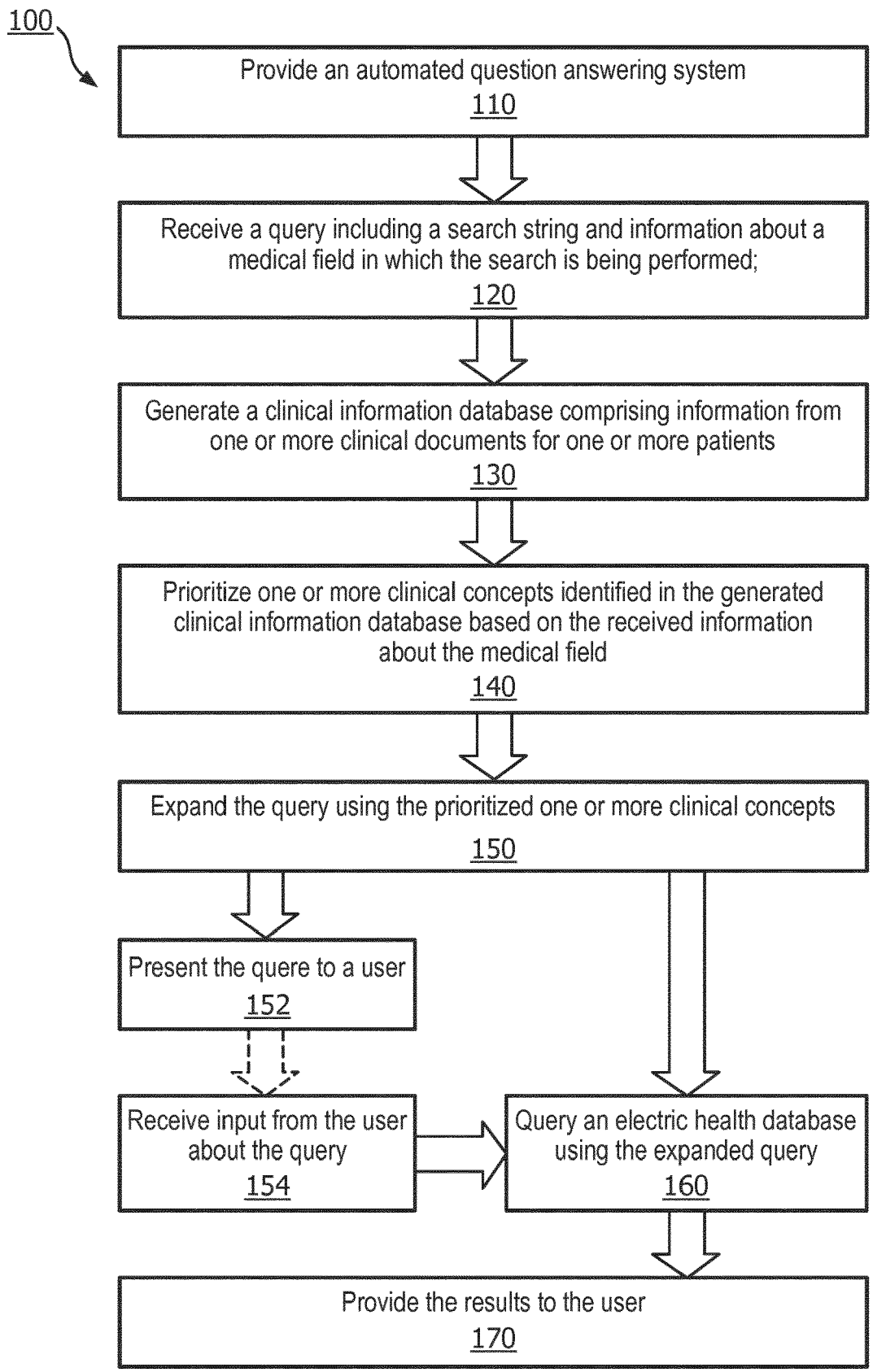
FIG. 1 is a flowchart of a method for query expansion, in accordance with an embodiment.

Referring to FIG. 1, in one embodiment, is a flowchart of a method 100 for an automated query expansion system. At step 110 of the method, an automated query expansion system is provided. The automated query expansion system may be any of the systems described or otherwise envisioned herein.

At step 120 of the method, a query is received from a user. The query may be received using any method or system, or from any source. For example, the query may be received from a user in real-time, such as from a user interface of a mobile device, laptop, desktop, wearable device, or any other computing device. The query may be received from any user interface that allows information to be received, such as a microphone or text input, among many other types of user interfaces. Alternatively, the query may be received from a computing device or an automated system. For example, a user's smartphone may be programmed to query the system.

The query may be received directly by the automated query expansion system, or may be received remotely and transmitted or otherwise communicated to the system. For example, the automated query expansion system may comprise a user interface that receives a query directly. Alternatively, the automated query expansion system may comprise a communications module that receives a query from any wired and/or wireless network, such as an intranet or the internet.

The query may take any form, and may include any words, terms, or acceptable characters. Examples of acceptable characters may be, for example, wildcard characters, grouping characters, escape characters, and/or operators. Examples of queries may include, for example: "phenomena" "depression" "heart disease" "family" "x-ray" "smok*" "smoker+nicotine" and many more.

At step 130 of the method, the system generates a clinical information model comprising information from one or more clinical documents for one or more patients. According to an embodiment, the information in the model comprises one or more clinical concepts identified or created during the generation of the model. The model may be created or otherwise modified in response to a query being received by the system, or may be created or otherwise modified prior to receipt of a query.

According to an embodiment, the system generates a multi-level clinical context model using a set of clinical information that depends on the type of search the user is making. For example, if the user intends to search the entire medical history of a patient, the set of clinical information may comprise clinical documents such as radiology/pathology reports, lab result, and an EMR problem list, for example. If the user is interested in an inter-patient search, the clinical information may comprise information about a single patient and/or specific clinical topics such as cardiology or urology. In either case, this model computes a multi-level clinical context model that provides a guide to the query expansion.

According to an embodiment, the system comprises a model creation module, which may be a processor, a component of one or more processors, and/or a software algorithm, which generates a clinical information model using a multi-level clinical context model pulling from raw clinical data. At least some of the clinical data is free-text clinical records such as handwritten notes from a clinician like a physician, nurse or other medical specialist.

According to an embodiment, the model creation module generates parses and compiles all the available clinical information, which may include structured and/or free-text documents, in the model or in the system where the search is being performed. Structured documents are reports, images, or document with predetermined or standard information, fields, or data entry. Free text documents are documents without standard data entry, and may include information such as handwritten notes or reports, or other non-standard information or reports. According to an embodiment, one or more clinical concepts are identified or created during the generation of the model, and these clinical concepts can be linked with one or more clinical ontologies such as SNOMED, ICD-10, and/or RadLex. According to an embodiment, the output of the model creation module is a list of clinical concepts in which each concept is linked to its original source of information. Each concept may also be linked with one or more clinical ontologies.

According to an embodiment, the model creation module stores the generated clinical information model in a database, which may be a component of the system or may be stored locally or remotely and in periodic and/or continuous communication with the system.

At step 150 of the method, the system prioritizes the one or more clinical concepts identified in the generated clinical information model. According to an embodiment, the one or more clinical concepts are prioritized based at least in part on information about the clinical context in which the search is being performed. The information about the clinical context in which the search is being performed can be received from the user as part of the query, or may be determined during creation of the clinical information model. Alternatively, the information about the clinical context in which the search is being performed may be determined based on the words used in the query, based on the person making the query (as certain users may be associated with certain clinical contexts), or based on one or more other parameters of the query, the system, the location, and/or the underlying data. According to an embodiment, the one or more clinical concepts are prioritized such that clinical concepts related to the identified clinical context are prioritized higher than clinical concepts unrelated to the identified clinical context.

According to an embodiment, the system comprises a prioritization module, which may be a processor, a component of one or more processors, and/or a software algorithm, which prioritizes the one or more clinical concepts identified in the generated clinical information model.

The one or more clinical concepts identified in the generated clinical information model can be prioritized according with the workflow in which the search is being performed. For a cardiology workflow, for example, concepts related with cardiac disease or diet and/or exercise habits could have higher priorities than the concepts related with a urology workflow. Optionally, a threshold can be used to eliminate concepts that does not reach a certain pre-establish priority level.

According to an embodiment, the prioritization module may utilize other information for prioritization. The other information may be utilized together with the identified clinical context for a single prioritization step, or the other information may be utilized before or after prioritization using the information about the identified clinical context. For example, the other information may include information about a received or determined clinical guideline or management plan. As an example, a clinical guideline may be specific for a department or hospital, or may be derived from an established organization such as the American College of Radiology or the American College of Cardiology, among many other examples. For example, Fleischner guidelines are used to manage solitary pulmonary nodules detected on a CT scanner. If a radiologist is reading a CT imaging study (workflow context) from a patient with history of pulmonary nodule (clinical context), concepts related to smoking, asbestos, and cancer family history will be prioritized since these concepts are relevant for the Fleischner guideline. These guidelines can be implemented by rules or other mechanisms that prioritize the one or more clinical concepts.

According to an embodiment, the output of the prioritization module is a list of one or more prioritized clinical concepts that can be utilized to expand the original search query.

Figure 2:
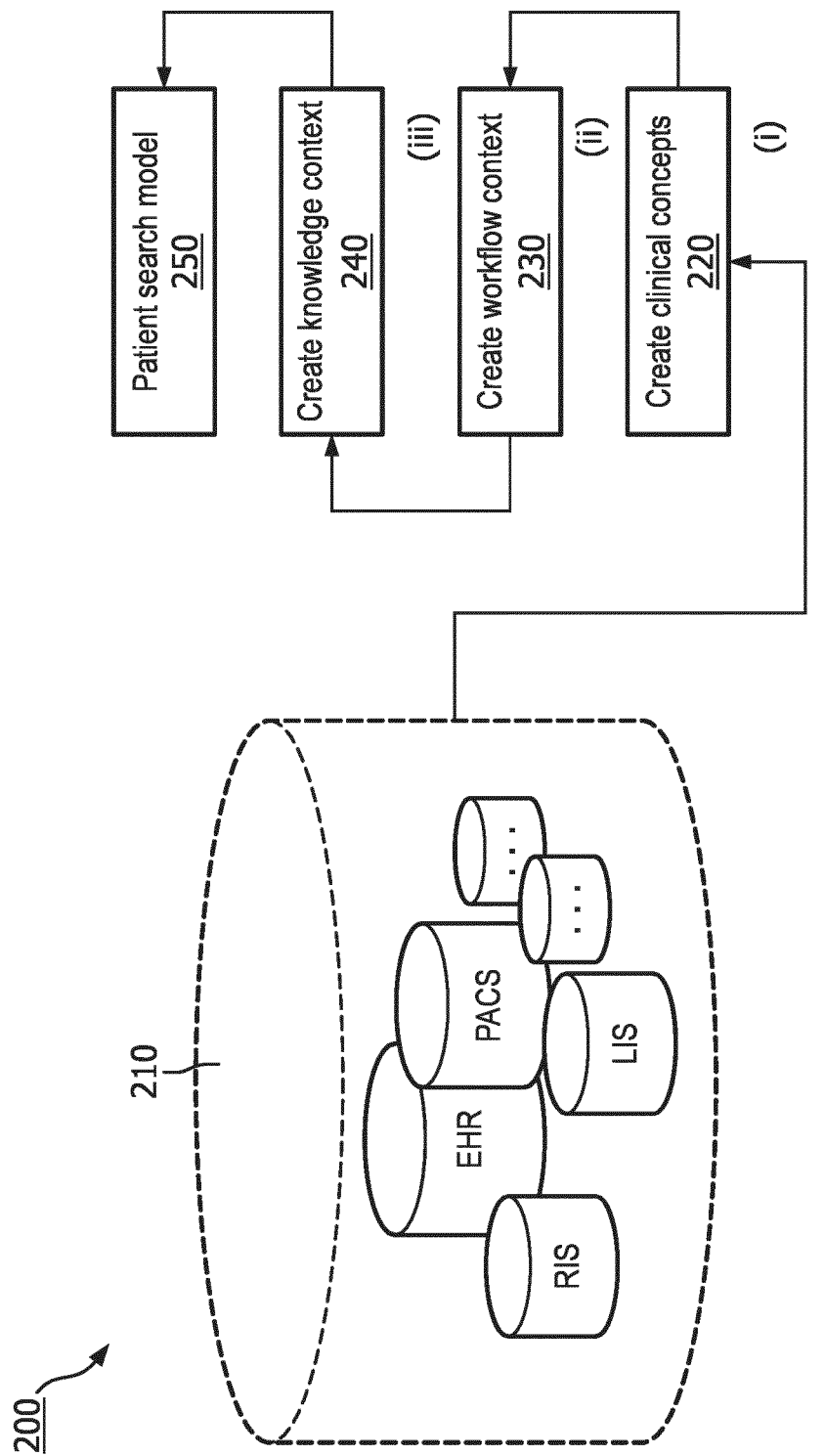
FIG. 2 is a schematic representation of a system or method for query expansion, in accordance with an embodiment.

Referring to FIG. 2, in one embodiment, is a schematic representation of a method or system 200 for generating the list of one or more prioritized clinical concepts, which can be utilized to expand an original search query. System or method 200 utilizes a corpus of information 210 such as electronic health records (EHR), information from a picture archiving and communication system (PACS), information from a radiology information system (RIS), and/or information from a laboratory information system (LIS), among many other sources of information. Corpus of information 210 may be internal to the organization or system, or may be external to the system or organization, or may be a combination of internal and external information sources. Corpus of information 210 may be in relation to or about a single patient, or it may be in relation to or about multiple patients.

At 220, the system or method extracts one or more clinical concepts from the corpus of information. For example, the system or method may utilize any of the methods or strategies described or otherwise envisioned herein, including but not limited to the model creation module.

At 230, the system or method creates a clinical workflow context. For example, the system may create the workflow context by prioritizing one or more clinical concepts extracted from the corpus of information. According to an embodiment, the one or more clinical concepts are prioritized based at least in part on information about the clinical workflow in which the search is being performed. For example, the system or method may utilize any of the methods or strategies described or otherwise envisioned herein, including but not limited to the prioritization module.

At 240, the system or method creates a knowledge context. According to an embodiment, the knowledge context comprises information about a received or determined clinical guideline or management plan, or about one or more medical and/or scientific publications. As an example, a clinical guideline may be specific for a department or hospital, or may be derived from an established organization. These guidelines or management plan can be implemented by rules or other mechanisms that prioritize the one or more clinical concepts. According to an embodiment, the one or more clinical concepts can be prioritized or re-prioritized based on the received or determined clinical guideline or management plan using any process or system described or otherwise envisioned herein, including but not limited to the prioritization module.

According to an embodiment, the output of system or method 200 is a patient search model comprising a list of prioritized concepts that can be used to expand the original search query.

At step 150 of the method in FIG. 1, the system expands the query utilizing the list of prioritized concepts created in step 140. The query can be expanded utilizing any method of query expansion, including but not limited to synonym-based expansion, topic model-based expansion, and/or predication-based model expansion. According to an embodiment, the output of step 150 is a list of terms or a search string which will be utilized to perform the query.

As an example, a user may perform an intra-patient search for the word "phenomena." The system may suggest, after performing steps 120-140 of the method, a list of clinical concepts such as 'Computed Tomography', 'mass' and 'smoke'. These clinical concepts may be based on, for example, the extracted clinical concepts, the information about the clinical workflow identified, and/or the information about a received or determined clinical guideline or management plan. During step 150 of the method, the system may utilize a query expansion technique to expand one or more of the clinical concepts in the list to produce an output list of prioritized clinical concepts such as 'X-ray', 'nodule', 'ground-grass', 'tobacco, and/or cigarette', among many others.

According to an embodiment, the system comprises a query expansion module, which may be a processor, a component of one or more processors, and/or a software algorithm, which expands the query utilizing any of the methods or systems described or otherwise envisioned herein.

At optional step 152 of the method, the system presents the expanded query to a user, including but not limited to the user that provided the original search string. The expanded query may be presented using any method or system. For example, the query may be presented to the user in real-time, such as via a user interface of a mobile device, laptop, desktop, wearable device, or any other computing device. The query may be presented by any user interface that allows information to be presented, such as a microphone or text input, among many other types of user interfaces. Alternatively, the query may be presented to a computing device or an automated system. According to an embodiment, the system presents the user with one or more concepts with a high assigned priority. The system may present the concept with one or more respective expansion terms identified by the system.

At optional step 154 of the method, the system receives input from the user regarding the provided expanded query. The input may be any modification of the expanded or original query, or may be an approval of the expanded query and/or an indication to perform the search. For example, the user may remove one or more concepts from the list or may change one or more priorities assigned by the system before the query is performed. This may further customize the expansion query for a specific user requirement, and may also improve the query expansion module via user feedback. As just one example, a radiologist may choose to add a "smoke history" expansion suggestion or search term if the radiologist is interested in investigating the imaging finding associated with a lung nodule.

At step 160 of the method, the system queries a database such as an electronic health database using the expanded query. According to an embodiment, the database is queries using any known method for querying a database, including but not limited to a query language such as SQL, NoSQL, or cypher, among many others.

At step 170 of the method, the system provides the results of the search to the user. The results of the search may be presented using any method or system. For example, the results of the search may be presented to the user in real-time, such as via a user interface of a mobile device, laptop, desktop, wearable device, or any other computing device. The results of the search may be presented by any user interface that allows information to be presented, such as a microphone or text input, among many other types of user interfaces. Alternatively, the results of the search may be presented to a computing device or an automated system.

According to an embodiment, the results of the search can be provided in a ranked format. For example, the results may be ranked based on the prioritization of the clinical concepts, and/or on the input received from the user regarding the expanded query.

Figure 3:
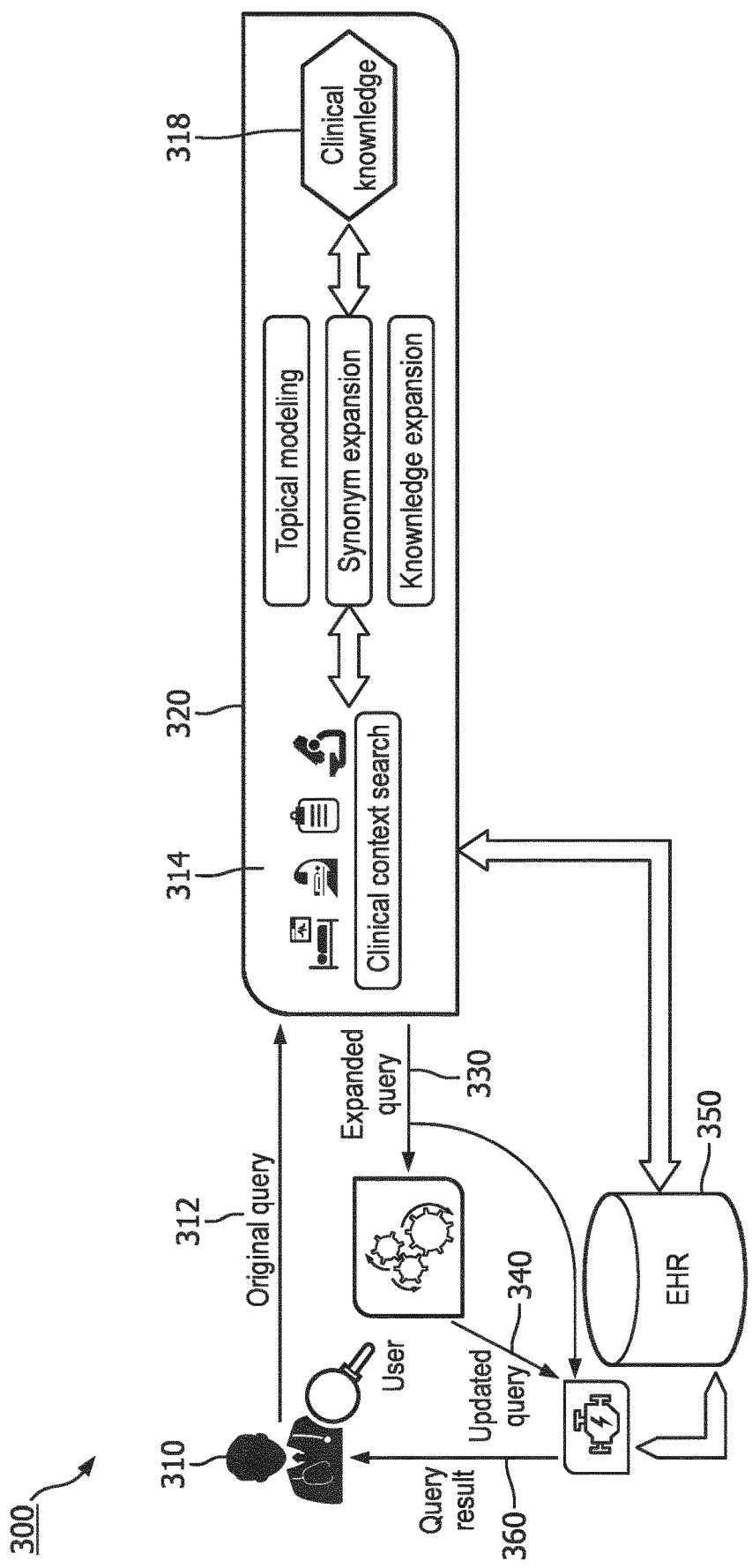
FIG. 3 is a schematic representation of a system or method for query expansion, in accordance with an embodiment.

Referring to FIG. 3, in one embodiment, is a schematic representation of a system 300 for searching a database using an expanded query. To initiate the process, a user 310 provides a query 312, such as through a user interface. The query may be, for example, about a particular patient and/or patient history or treatment. The system generates a patient search model 320 utilizing information extracted about clinical concepts 314, information about the clinical workflow 318 in which the search is being performed, and/or information about a clinical guideline or management plan for the patient.

The patient search model 320 is utilized to generate an expanded query 330, which is optionally provided to user 310 via a user interface. The user may modify, reject, or approve the expanded query 330. Alternatively, the expanded query 330 may bypass user review.

The expanded query 330 or a modified version of the expanded query 340 it then utilized to query a database 350 such as an electronic health record database. The query results 360 are presented to the user, such as through a user interface.

Figure 4:
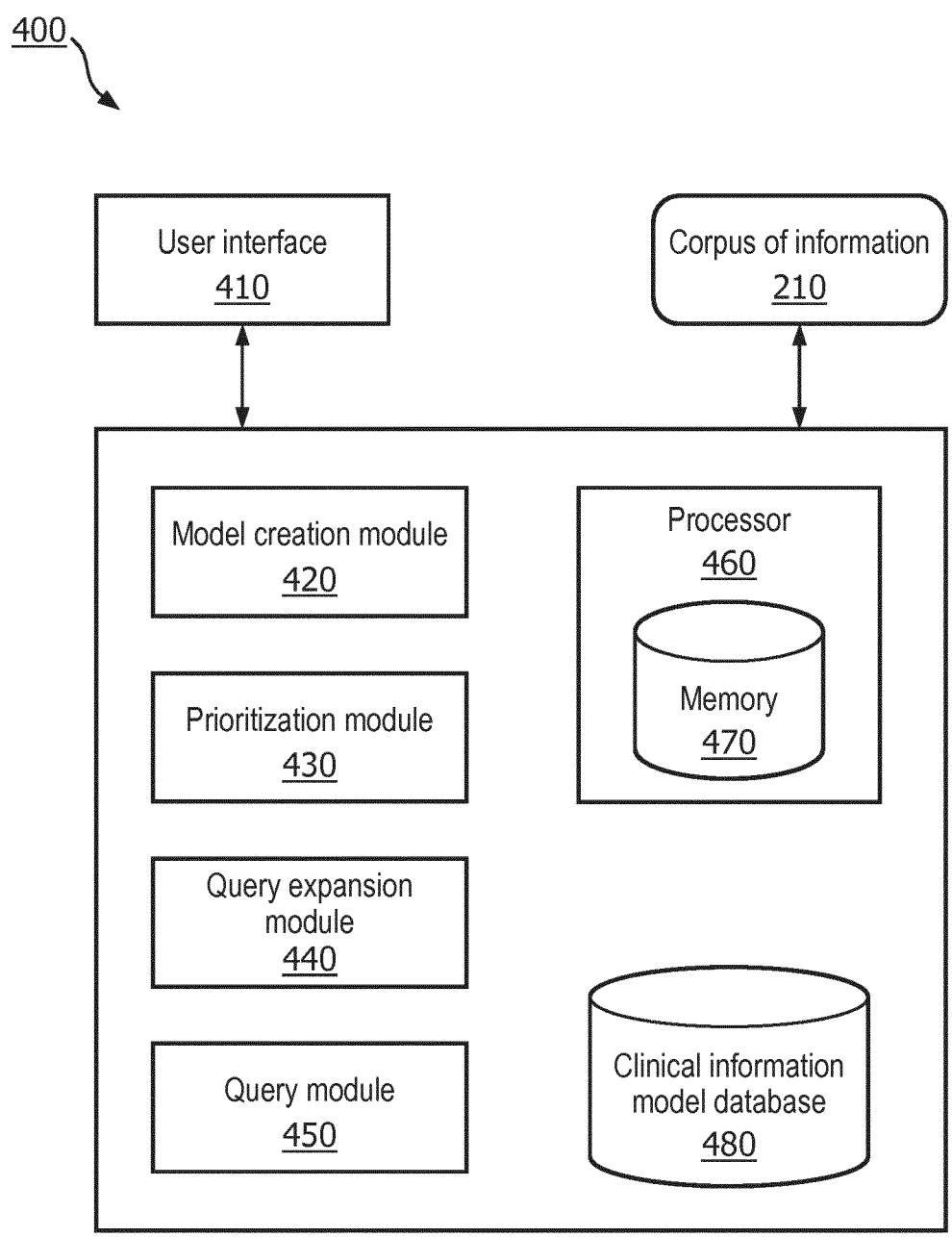
FIG. 4 is a schematic representation of a system for query expansion, in accordance with an embodiment.

Referring to FIG. 4, in one embodiment, is a schematic representation of a system 400 for generating an expanded search query. System 400 can comprise any of the elements, databases, processors, and/or other components described or otherwise envisioned herein.

According to an embodiment, system 400 comprises a user interface 410 to receive a query, provide an expanded query to the user, and/or to provide the results of a search to the user. The user interface can be any device or system that allows information to be conveyed and/or received, such as a speaker or screen, among many other types of user interfaces. The information may also be conveyed to and/or received from a computing device or an automated system. The user interface may be located with one or more other components of the system, or may located remote from the system and in communication via a wired and/or wireless communications network.

According to an embodiment, system 400 comprises or is in communication with or is in receipt of a corpus of information 210 such as electronic health records (EHR), information from a picture archiving and communication system (PACS), information from a radiology information system (RIS), and/or information from a laboratory information system (LIS), among many other sources of information. Corpus of information 210 may be internal to the organization or system, or may be external to the system or organization, or may be a combination of internal and external information sources. Corpus of information 210 may be in relation to or about a single patient, or it may be in relation to or about multiple patients.

System 400 comprises a model creation module 420, which may be a processor, a component of one or more processors, and/or a software algorithm. The model creation module generates a clinical information model comprising information from one or more clinical documents for one or more patients. According to an embodiment, the information in the model comprises one or more clinical concepts identified or created during the generation of the model. The model may be created or otherwise modified in response to a query being received by the system, or may be created or otherwise modified prior to receipt of a query. At least some of the clinical data is free-text clinical records such as handwritten notes from a clinician like a physician, nurse or other medical specialist.

According to an embodiment, the model creation module 420 stores the generated clinical information model in a database 480, which may be a component of the system or may be stored locally or remotely and in periodic and/or continuous communication with the system.

System 400 comprises a prioritization module 430, which may be a processor, a component of one or more processors, and/or a software algorithm. The prioritization module 430 prioritizes the one or more clinical concepts identified in the generated clinical information model. According to an embodiment, the one or more clinical concepts are prioritized based at least in part on information about the clinical context in which the search is being performed, and/or on information about a received or determined clinical guideline or management plan.

According to an embodiment, the one or more clinical concepts are prioritized based at least in part on information about the clinical context in which the search is being performed. The information about the clinical context in which the search is being performed can be received from the user as part of the query, or may be determined during creation of the clinical information model. Alternatively, the information about the clinical context in which the search is being performed may be determined based on the words used in the query, based on the person making the query (as certain users may be associated with certain clinical contexts), or based on one or more other parameters of the query, the system, the location, and/or the underlying data. According to an embodiment, the one or more clinical concepts are prioritized such that clinical concepts related to the identified clinical context are prioritized higher than clinical concepts unrelated to the identified clinical context.

According to an embodiment, the information about a received or determined clinical guideline or management plan may be specific for a department or hospital, or may be derived from an established organization such as the American College of Radiology or the American College of Cardiology, among many other examples. These guidelines can be implemented by rules or other mechanisms that prioritize the one or more clinical concepts.

System 400 comprises a query expansion module 440, which may be a processor, a component of one or more processors, and/or a software algorithm. The query expansion module 440 expands the query utilizing the list of prioritized concepts. The query can be expanded utilizing any method of query expansion, including but not limited to synonym-based expansion, topic model-based expansion, and/or predication-based model expansion. According to an embodiment, the output of the query expansion module 440 is a list of terms or a search string which will be utilized to perform the query.

A query module 450, which may be a processor, a component of one or more processors, and/or a software algorithm. The query module 450 queries a database such as an electronic health database using the expanded query. According to an embodiment, the database is queries using any known method for querying a database, including but not limited to a query language such as SQL, NoSQL, or cypher, among many others. The query module or another component or module may rank the results of the query based on, for example, the prioritization of the clinical concepts, and/or on the input received from the user regarding the expanded query. The query module or another component or module may then provide the results of the search to the user. The results of the search may be presented using any method or system, such as user interface 410.

According to an embodiment, system 400 comprises a processor 460 which performs one or more steps of the method, and may comprise one or more of the modules. Processor 460 may be formed of one or multiple modules, and can comprise, for example, a memory 470. Processor 460 may take any suitable form, including but not limited to a microcontroller, multiple microcontrollers, circuitry, a single processor, or plural processors. Memory 470 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by the processor, controls operation of one or more components of system 400.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used.

Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A system configured to generate an expanded query for a health database, the system comprising:
    a user interface configured to receive a query from a user, wherein the query comprises a search string and information about a clinical context in which the query is being performed; and
    a hardware processor comprising:
        a model creation module configured to generate a clinical information model comprising information from one or more clinical documents for one or more patients, wherein the information from the one or more clinical documents comprises a plurality of clinical concepts;
        a prioritization module configured to prioritize the plurality of clinical concepts identified in the generated clinical information model based on at least: (i) the received information about the clinical context in which the query is being performed; and (ii) a clinical guideline or management plan for the patient, wherein clinical concepts related to the clinical context, or to the clinical guideline or management plan, are prioritized higher than clinical concepts unrelated to the clinical context, wherein the plurality of clinical concepts are ranked based on at least a prioritization of the clinical concepts;
        a query expansion module configured to create an expanded query using the prioritized one or more clinical concepts, wherein a highest ranked term is utilized to expand the original query; and
        a query module configured to query the health database using the expanded query.

2. The system of claim 1, wherein at least some of the one or more clinical documents are free-text documents.

3. The system of claim 1, wherein at least some of the one or more clinical documents are structured medical documents.

4. The system of claim 1, wherein the clinical information model is generated using natural-language processing.

5. The system of claim 1, wherein the clinical information model is limited to records about a single patient.

6. The system of claim 1, wherein the query expansion module is configured to expand the query utilizing one or more of synonym-based expansion, topic model-based expansion, and predication-based model expansion.

7. The system of claim 1, wherein the user interface is further configured to provide the expanded query to a user, and further configured to receive information from the user about the expanded query.

8. The system of claim 7, wherein the information received from the user modifies the expanded query.

9. The system of claim 1, wherein the clinical guideline or management plan is a clinical guideline or management plan that has been assigned to the patient.

10. A method for querying a health database using an expanded query generation system comprising a user interface and a hardware processor, the method comprising the steps of:
- receiving a query from a user via the user interface, wherein the query comprises a search string and information about a clinical context in which the query is being performed;
- generating, by the hardware processor, a clinical information model comprising information from one or more clinical documents for one or more patients, wherein the information from the one or more clinical documents comprises a plurality of clinical concepts;
- prioritizing, by the hardware processor, the plurality of clinical concepts identified in the generated clinical information model based on at least: (i) the received information about the clinical context in which the query is being performed; and (ii) a clinical guideline or management plan for the patient, wherein clinical concepts related to the clinical context, or to the clinical guideline or management plan, are prioritized higher than clinical concepts unrelated to the clinical context;
- ranking the plurality of clinical concepts based on at least a prioritization of the clinical concepts;
- expanding, by the hardware processor, the query using the prioritized one or more clinical concepts to create an expanded query, wherein a highest ranked term is utilized to expand the original query; and
- querying the health database using the expanded query.

11. The method of claim 10, further comprising the step of providing results of the health database query to the user.

12. The method of claim 10, further comprising the steps of:
- providing the expanded query to the user via the user interface; and
- receiving input from the user regarding the expanded query, wherein the input modifies the expanded query.

13. The method of claim 10, wherein at least some of the one or more clinical documents are free-text documents.

14. The method of claim 10, wherein at least some of the one or more clinical documents are structured medical documents.

15. The method of claim 10, wherein the clinical information model is limited to records about a single patient.

16. The method of claim 10, wherein the query is expanded utilizing one or more of synonym-based expansion, topic model-based expansion, and predication-based model expansion.

* * * * *